United States Patent [19]

Deckner

[11] Patent Number: 4,481,186

[45] Date of Patent: Nov. 6, 1984

[54] NON-IRRITATING COSMETIC COMPOSITION CONTAINING GLUCAMINE FATTY ACID EMULSIFIER SOAP

[75] Inventor: George E. Deckner, Westfield, N.J.

[73] Assignee: Charles of the Ritz Group Ltd., New York, N.Y.

[21] Appl. No.: 499,057

[22] Filed: May 27, 1983

[51] Int. Cl.$^3$ .......................... A61K 7/15; A61K 7/42; A61K 7/44; A61K 31/16
[52] U.S. Cl. .......................................... 424/59; 424/60; 424/63; 424/238; 424/274; 424/284; 424/320; 424/357; 424/358; 424/361; 424/362; 424/363; 424/365
[58] Field of Search .................... 424/59, 361, 63, 60; 260/404, 404.5

[56] References Cited

U.S. PATENT DOCUMENTS

| | | | |
|---|---|---|---|
| 4,137,302 | 1/1979 | Humbert et al. | 424/63 |
| 4,146,649 | 3/1979 | Siegel | 424/361 |
| 4,159,318 | 6/1979 | Mausner et al. | 424/63 |

FOREIGN PATENT DOCUMENTS

| | | | |
|---|---|---|---|
| 15030 | 9/1980 | European Pat. Off. | 424/361 |
| 39860 | 11/1981 | European Pat. Off. | 424/361 |
| 1948990 | 5/1970 | Fed. Rep. of Germany | 424/361 |
| 3017814 | 11/1981 | Fed. Rep. of Germany | 424/361 |
| 1540187 | 7/1968 | France | 424/59 |
| 147937 | 1/1963 | Japan | 424/361 |
| 36412 | 3/1980 | Japan | 424/361 |

OTHER PUBLICATIONS

Chem. Abs., vol. 92, 1980, p. 220543u, Hoffenberg, p. 315.
Chem. Abs., vol. 92, 1980, p. 169053e, Honda et al., p, 333, 169055g.
Chem. Abs., vol. 94, 1981, 109080t, Szego et al., p. 381.
Chemical Abstracts, 88:126184y, 95:175573c, 95:138393y, 93:173621b.

Primary Examiner—Dale R. Ore
Attorney, Agent, or Firm—Lawrence S. Levinson; Burton Rodney

[57] ABSTRACT

Cosmetic and skin treatment compositions are provided which include as an emulsifier a glucamine-fatty acid soap. The glucamine fatty acid salt aids in forming stable emulsions without causing undue irritation to skin.

12 Claims, No Drawings

NON-IRRITATING COSMETIC COMPOSITION CONTAINING GLUCAMINE FATTY ACID EMULSIFIER SOAP

FIELD OF THE INVENTION

The present invention relates to cosmetic and skin treatment compositions which contain as an emulsifier a glucamine-fatty acid soap.

BACKGROUND OF THE INVENTION

Effective cosmetic and skin treatment compositions are expected to immprt a supple moist condition to the skin. This is achieved, in part, by providing such compositions in the form of soothing, non-irritating, stable, oil-in-water emulsions.

Many make-up or other cosmetic compositions contain triethanolamine and stearic acid which react in situ in the cosmetic composition to form an emulsifier which has been found to be effective and acceptable. However, the potential exists for development of skin irritation problems if too much triethanolamine stearic acid emulsifier is employed over extended periods of time.

BRIEF DESCRIPTION OF THE INVENTION

It has now surprisingly been found that cosmetic and skin care compositions may be formulated as soothing stable emulsions without the need for employing triethanolamine. Such emulsions are prepared using glucamine-fatty acid soaps in place of triethanolamine-fatty acid salts. Cosmetic and skin care formulations containing the glucamine-fatty acid soaps will be superior to similar formulations containing triethanolamine-fatty acid salts in that such soaps are less irritating to the skin than the above salts.

DETAILED DESCRIPTION OF THE INVENTION

In accordance with the present invention, there is provided improved cosmetic and skin care and treatment compositions which contain as an essential emulsifier ingredient one or more soaps formed from glucamine and a fatty acid containing from 10 to 30 carbon atoms and preferably from 12 to 20 carbon atoms.

Examples of long chain fatty acids which may be employed herein include but are not limited to saturated monocarboxylic acids such as lauric acid, tridecanoic acid, myristic acid, pentadecanoic acid, palmitic acid, margaric acid, stearic acid, nonadecanoic acid, arachidic acid, heneicosanoic acid, behenic acid, tricosanoic acid, tetracosanoic acid, pentacosanoic acid, cerotic acid and the like, as well as arachidonic acid, oleic acid, isostearic acid, ricinoleic acid, and hydroxystearic acid. Preferred fatty acids are stearic acid, lauric acid, myristic acid and palmitic acid.

The glucamine-fatty acid soap may be formed in situ in the cosmetic formulation, that is, each of the glucamine and fatty acid is added separately and the soap formed in situ. However, if desired, the glucamine-fatty acid soap may be formed by simply mixing the separate glucamine and fatty acid in stoichiometric proportions and added as the soap to the cosmetic ingredients.

The cosmetic formulations and skin care and treatment formulations of the invention will contain from about 0.1 to about 5% and preferably from about 0.5 to about 1.5% by weight of glucamine based on the total weight of the cosmetic formulation and from about 1 to about 10% and preferably from about 2 to about 4% by weight fatty acid, based on the total weight of the cosmetic formulation. Thus, the glucamine will preferably be employed in a weight ratio to the fatty acid of within the range of from about 0.1:1 to about 0.5:1 and more preferably from about 0.25:1 to about 0.4:1.

The make-up or cosmetic formulation of the invention may also contain an acetylated phytosterol, namely, a blend of acetylated sitosterol, acetylated campesterol, acetylated stigmasterol and possibly acetylated cholesterol, in an amount within the range of from about 0.1 to about 10% by weight and preferably from about 1 to about 2% by weight.

The cosmetic and skin treatment formulations of the invention will also contain conventional cosmetic ingredients necessary in formulating a desirable product, such as, one or more diluents, thickeners, stabilizers, coloring agents, humectants, preservatives, emollients, bodying agents, sunscreen agents and the like. Thus, the formulations of the invention may contain one or more diluents such as deionized water in an amount within the range of from about 40 to about 90% and preferably from about 50 to about 80% by weight, optionally one or more thickeners, such as magnesium aluminum silicate and xanthan gum in an amount within the range of from about 0.1 to about 2% and preferably from about 0.1 to about 0.5% by weight, in the case of cosmetic or make-up formulations one or more coloring agents or pigments such as titanium dioxide, various iron oxides, ultramarine blue and the like totaling from about 10 to about 15% by weight, skin protecting agents, such as panthenol, which serves as a skin moisturizer and humectant, in an amount within the range of from about 0.1 to about 5% and preferably from about 0.1 to about 1% by weight, one or more other humectants such as polyethylene glycols (for example, Carbowax 400), sodium 2-pyrrolidone carboxylic acid, sorbitol, propylene glycol or glycerine in an amount within the range of from about 1 to about 20% and preferably from about 1 to about 5% by weight, one or more preservatives such as parabens including methyl paraben, propyl paraben, butyl paraben, Glydant (dimethyldimethoyl hydantoin), benzyl alcohol, imidazolidinyl urea and the like usually employed in amounts within the range of from about 0.1 to about 1% by weight and preferably from about 0.5 to about 0.8% by weight, one or more emollients or emollient oils such as mineral oil, avocado oil, petrolatum, propylene glycol dicaprylate/dicaprate, and isopropyl myristate in an amount within the range of from about 10 to about 20% by weight and preferably from about 10 to about 15% by weight, one or more co-emulsifiers such as PEG 20 sorbitan monolaurate (Polysorbate 20), diethanolamine cetyl phosphate, glyceryl stearate, polyethylene glycol 100 stearate, and PEG 20 stearyl ether (Brij 78, Steareth 20) PEG 150 distearate in an amount within the range of from about 0.1 to about 2% by weight and preferably from about 0.2 to about 1% by weight; one or more bodying agents such as stearic acid, glyceryl monostearate, and the like in an amount within the range of from about 1 to about 10% by weight and preferably from about 1 to about 5% by weight, optionally one or more sun screen agents such as octyl dimethyl p-aminobenzoic acid, octyl salicylate, benzophenone 3 and the like in an amount within the range of from about 0.5 to about 10% by weight and preferably from about 1 to about 5% by weight, and optionally one or more antioxidants such as dl-alpha-tocopherol in an amount within the range of from about 0.05 to about 0.5% by weight and preferably from about 0.05 to about 0.2% by weight. In addition, the formulations of the invention may contain one or more fragrances, solubilizing agents and emulsifiers for the fragrances such as polyoxyethylene (13) octyl phenyl ether.

The cosmetic formulation of the invention may be prepared as follows.

Deionized water (diluent) together with thickener/stabilizer such as magnesium aluminum silicate are mixed together to form a first mixture (A). Then, one or ore emulsifiers and/or wetting agents are added. Coloring agents or pigments are mixed therewith until completely dispersed to form mixture (AB). A clear aqueous solution of skin protecting agent such as dl-panthenol (Phase C) (where present) is mixed with mixture AB. The new mix ABC is then mixed with a mixture of humectant such as a Carbowax, preservative such as a paraben and thickener such as xanthan gum (Phase D) to form mix ABCD. Aqueous glucamine is then added with mixing to form mix (A-E). Thereafter preservatives such as one or more parabens, emollients including acetylated sterol, antioxidant such as dl-alpha-tocopherol, sunscreens and emulsifiers (fatty acid which forms soap in situ with glucamine) are mixed together and combined with the mixture (A-F). Then a preservative such as imidazolidinyl urea (Germall 115) is added to the above mix to form the cosmetic formulation of the invention. The so-formed mix is cooled to form the cosmetic formulation of the invention.

The following Example represents preferred embodiments of the invention.

EXAMPLE 1

A soothing make-up having the following composition was prepared as described below.

| Ingredient | Parts by Weight |
| --- | --- |
| Phase A | |
| Deionized water | 48 |
| Veegum R (magnesium aluminum silicate) (thickener) | 1 |
| Alcolec 4135 (lecithin, polysorbate 20, sorbitan laurate and propylene glycol stearate and propylene glycol laurate) (emulsifier wetting agent) | 1 |
| Phase B | |
| Kaolin 2749 (skin protectant) | 4 |
| Umber 1985R | 0.5 |
| Russet C33-2527 | 0.3 |
| Yellow 2576 | 1 |
| Blue 3516 | 0.01 |
| TiO2 water dispersable (90% TiO2, 10% Talc) | 10 |
| Phase C | |
| Deionized water | 1 |
| dl-Panthenol (skin protectant) | 0.5 |
| Phase D | |
| Carbowax 400 (humectant) | 4.5 |
| Tegosept P (propyl paraben) (preservative) | 0.2 |
| Keltrol F (xanthan gum) (thickener) | 0.2 |
| Phase E | |
| Deionized water | 2 |
| Glucamine (emulsifier) | 1 |
| Phase F | |
| Tegosept P (propyl paraben) (preservative) | 0.1 |
| Butoben (butyl paraben) (preservative) | 0.1 |

-continued

| Ingredient | Parts by Weight |
| --- | --- |
| Klearol (mineral oil) (emollient) | 5 |
| Miglyol 840 (propylene glycol dicaprylate/tricaprate) (emollient) | 6 |
| Stearic acid (emulsifier, thickener) | 3.5 |
| Tegin 515 (glyceryl monostearate) (auxiliary emulsifier, thickener) | 2.5 |
| Escalol 507 (octyl dimethyl p-amino benzoic acid) (sunscreen) | 2.5 |
| Uvinol M-40 (benzophenone 3) (sunscreen) | 0.5 |
| Phyosterol Acetate (acetylated sitosterol-about 56% acetylated campesterol-about 28% acetylated stigmasterol-about 4%) | 1 |
| Silicone 225 (emollient) | 1.5 |
| Avocado oil (emollient) | 0.5 |
| PEG-6000 distearate (emulsifier thickener) | 0.2 |
| Vitamin E, dl alpha-tocopherol (antioxidant) | 0.1 |
| Phase G | |
| Deionized water | 0.75 |
| Germall 115 (preservative) | 0.25 |
| Phase H | |
| Carbowax 400 (humectant) | 0.5 |
| Exaltolide (pentadecalactone) (odor masking agent) | 0.5 |

The Phase A ingredients were homomixed for 15 minutes. Thereafter, a mix of the Phase B ingredients were added to the Phase A mixture with homomixing for 1 hour.

Phase C was then mixed with Phase AB for 5 minutes under slow speed mixing. Phase D was then added to the aforementioned mix with mixing for ½ hour. Phase E was then added and the so-formed mix was then heated to 75° C. While maintaining the mix at 75° C., Phase F was heated to 80° C., and was then added to the above mix with fast mixing to form an emulsion. The mix was then mixed with moderate speed for ½ hour and slowly cooled to 50° C. and then combined with Phase G and mixed for 5 minutes. Thereafter Phase H was added and the mixture was cooled to 30° C. to form the make-up of the invention. The so-formed make-up of the invention was found to be soothing, non-irritating and noncomedongenic.

EXAMPLE 2

A soothing skin treatment preparation having the following composition was prepared as described below.

| Ingredient | Parts by Weight |
| --- | --- |
| Phase A | |
| Deionized water | 77 |
| Na2EDTA (chelating agent) | 0.05 |
| Carbopol 934 (carboxyvinyl polymer) | 0.2 |
| Glycerin (humectant) | 4 |
| Phase B | |
| Carbowax 400 (humectant) | 1 |
| Methyl paraben (preservative) | 0.2 |
| Keltrol F (xanthan gum) (thickener) | 0.1 |
| Phase C | |
| Deionized water | 2 |
| Glucamine (emulsifier) | 1 |
| Phase D | |
| Tegosept P (propyl paraben) (preservative) | 0.1 |
| Satulan (hydrogenated lanolin) | 0.5 |

-continued

| Ingredient | Parts by Weight |
| --- | --- |
| (auxiliary emulsifier) | |
| Klearol (mineral oil) (emollient) | 8 |
| Stearic acid (emulsifier, thickener) | 2 |
| Tegin 515 (glyceryl monostearate) (auxiliary emulsifier, thickener) | 0.9 |
| Escalol 507 (octyl dimethyl p-amino benzoic acid) (sunscreen) | 2 |
| Uvinol M-40 (benzophenone 3) (sunscreen) | 0.5 |
| Phase E | |
| Glydant (dimethyldimethoyl hydantoin) (preservative) | 0.3 |

The Phase A ingredients were homomixed for 15 minutes.

Phase B was then added and was sweep mixed therein for 15 minutes. The so-formed mix was then heated to 75° C. While maintaining the mix at 75° C., Phase C was added. Phase D, heated at 80° C., was then added to the above mix with fast mixing to form an emulsion. The mix was then mixed with moderate speed, cooled to 50° C. and then combined with Phase E and mixed for 5 minutes. The mixture was cooled to 30° C. to form the make-up of the invention.

During the above process, the glucamine neutralizes the carboxyvinyl polymer and forms a soap in situ with stearic acid.

The so-formed make-up of the invention was found to be soothing, non-irritating and noncomedongenic.

What is claimed is:

1. A non-irritating cosmetic or soothing "Moisturizing and conditioning" skin composition consisting essentially of a non-irritating glucamine-fatty acid emulsifier soap formed of from about 0.1 to about 5% by weight glucamine and from about 1 to about 10% by weight of a fatty acid containing 10 to 30 carbons, 40 to 90% water, "At least one thickener, at least one humectant" and at least one preservative.

2. The skin composition as defined in claim 1 including at least one coloring agent or pigment.

3. The skin composition as defined in claim 1 wherein the glucamine and fatty acid form a soap in situ.

4. The skin composition as defined in claim 1 wherein the glucamine and fatty acid are in the form of a preformed soap.

5. The skin composition as defined in claim 1 wherein the fatty acid is lauric acid, stearic acid, myristic acid, oleic acid, isostearic acid, hydroxystearic acid, or behenic acid.

6. The skin composition as defined in claim 1 further including acetylated soya bean derived sterol which includes acetylated sitosterol, acetylated campesterol, acetylated stigmasterol, acetylated cholesterol or mixtures thereof.

7. The skin composition as defined in claim 3 wherein the acetylated soya bean derived sterols is a mixture of acetylated sitosterol, acetylated campesterol and acetylated stigmasterol.

8. The skin composition as defined in claim 1 further including at least one antioxidant, at least one bodying agent selected from the group consisting of stearic acid and glyceryl monostearate, and at least one thickener selected from the group consisting of magnesium aluminum silicate and xanthan gum, and panthenol.

9. The skin composition as defined in claim 1 further including at least one sun screen agent selected from the group consisting of octyl dimethyl p-aminobenzoic acid, octyl salicylate and benzophenone.

10. The skin composition as defined in claim 1 further including at least one co-emulsifier selected from the group consisting of polyethylene glycol sorbitan monolaurate, diethanolamine cetyl phosphate, glyceryl stearate, polyethylene glycol stearyl ether and polyethylene glycol distearate.

11. The skin composition as defined in claim 1 further including at least one emollient or emollient oil selected from the group consisting of mineral oil, avocado oil, petrolatum, propylene glycol dicaprylate/dicaprate and isopropyl myristate.

12. The skin composition as defined in claim 1 "Wherein said humectant is" selected from the group consisting of panthenol, a polyethylene glycol, sodium 2-pyrrolidone carboxylic acid, sorbitol, propylene glycol or glycerine.

* * * * *

UNITED STATES PATENT AND TRADEMARK OFFICE
CERTIFICATE OF CORRECTION

PATENT NO. : 4,481,186
DATED : November 6, 1984
INVENTOR(S) : George E. Deckner

It is certified that error appears in the above-identified patent and that said Letters Patent is hereby corrected as shown below:

Column 3, line 12, "ore" should read -- more --.

Column 5, lines 35 and 36, "soothing "Moisturizing and conditioning" skin" should read -- soothing moisturizing and conditioning skin --.

Column 5, lines 41 and 42, "water, "At least one thickener, at least one humectant" and " should read -- water, at least one thickener, at least one humectant and --.

Column 6, line 41, should read -- wherein said humectant is selected from the group --.

Signed and Sealed this

Fourteenth Day of May 1985

[SEAL]

Attest:

DONALD J. QUIGG

Attesting Officer   Acting Commissioner of Patents and Trademarks